United States Patent [19]  [11] 4,322,416
Metcalf et al.  [45] Mar. 30, 1982

[54] 10-ALKYNYL STEROIDS

[75] Inventors: Brian W. Metcalf, Mason; J. O'Neal Johnston, Milford, both of Ohio

[73] Assignee: Merrell Dow Pharmaceuticals Inc., Cincinnati, Ohio

[21] Appl. No.: 258,214

[22] Filed: Apr. 27, 1981

Related U.S. Application Data

[63] Continuation-in-part of Ser. No. 163,451, Jun. 27, 1980, abandoned.

[51] Int. Cl.$^3$ .......................... A61K 31/56; C07J 1/00
[52] U.S. Cl. .................... 424/242; 424/243; 260/239.55 C; 260/239.55 R; 260/397.3; 260/397.4
[58] Field of Search .................... 424/242; 260/397.3, 260/397.4

[56] References Cited

U.S. PATENT DOCUMENTS 3,127,427  3/1964  Boller et al. .................. 260/397.3
3,218,316 11/1965  Edwards .................... 260/239.5

OTHER PUBLICATIONS

Tetrahedron Letters No. 23 (1979), pp. 2105–2108, relied on Article by D. F. Covey et al.
J. Biol. Chem., No. 256 (1981), p. 1076, Article by D. F. Covey et al.

Primary Examiner—Elbert L. Roberts
Attorney, Agent, or Firm—John J. Kolano; Raymond A. McDonald; Gary D. Street

[57] ABSTRACT

Aromatase inhibitors are provided having the formula

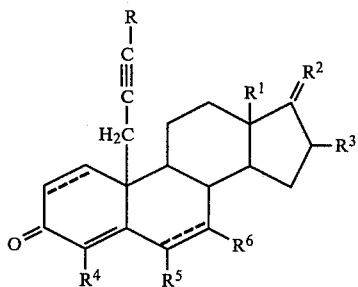

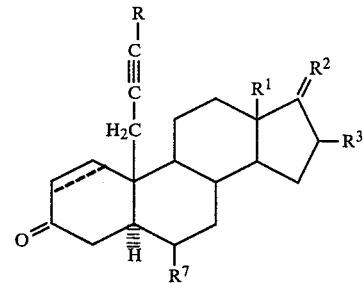

wherein ≈≈≈ represents a single or double bond; R is hydrogen or $C_{1-4}$ alkyl; $R^1$ is methyl or ethyl; $R^2$ is (H)($OR^8$) or =O; $R^3$ is H or $C_{1-3}$ alkyl; $R^4$ is H or $OR^8$; $R^5$ is H, $C_{1-3}$ alkyl or, when the 5,6-bond is saturated, $R^5$ is divalent =O; $R^6$ and $R^7$ are each H or $C_{1-3}$ alkyl; and $R^8$ is H or $C_{2-4}$ alkanoyl. Intermediates useful in preparing the foregoing aromatase inhibitors, and methods of using the aromatase inhibitors of the invention are also provided.

25 Claims, No Drawings

10-ALKYNYL STEROIDS

The present application is a continuation-in-part of Application Ser. No. 163,451, filed June 27, 1980 now abandoned.

BACKGROUND OF THE INVENTION

The female sex hormones estrone and estradiol are involved in many physiological processes and have been studied extensively. The formation of these steroids is regulated by a number of enzymes. The enzyme aromatase is the rate limiting enzyme in the conversion of testosterone and androstenedione (male hormones, androgens) to estradiol and estrone (female hormones, estrogens). The non-reversible conversion of these androgens to the estrogens involves the oxidation and elimination of the methyl groups at C-10 as formic acid. The 1β- and 2β-hydrogens from C-1 and C-2 are lost with the formation of a double bond so that, after enolization of the 3-ketone, the aromatic A-ring of the estrogens is produced. The androgens, testosterone and androstenedione, can be interconverted by 17β-hydroxysteroid dehydrogenase and the estrogens, estradiol and estrone, can be interconverted similarly (Scheme 1). Materials, such as aromatase inhibitors that regulate the androgen to estrogen conversion or inhibit this conversion have therapeutic utility in treating clinical conditions which are potentiated by the presence of the estrogens. Such aromatase inhibitors have been identified using microsomal enzyme preparations from human placenta and 4-hydroxy- and 4-acetoxy-androst-4-ene-3,17-dione, androsta-1,4,6- triene-3,17-dione, aminoglutethimide and testololactone have been identified as aromatase inhibitors.

ated with oligospermia which results from elevated estrogen levels. Aromatase inhibitors can also be used in treating hyperestrogenemia which may precede myocardial infarction.

Aromatase inhibitors are also useful in fertility control where they would be effective by reducing the estrogen surges observed at various stages of the ovulatory cycle. Thus, 4-acetoxyandrost-4-ene-3,17-dione has been found effective in preventing estrogen production required for ovulation in rats. In addition, since estrogen synthesis is necessary for implantation of fertilized ova in many species, post-coital administration of aromatase inhibitors has the potential to regulate fertility, particularly in domestic pets and wildlife. In particular, the aromatase inhibitor androsta-1,4,6-triene-3,17-dione has been found effective in preventing implantation in mated rats. Aromatase inhibitors should also reduce mating behavior of male species which require brain aromatization for such behavior. In particular, suppression of rodent reproduction has been effective by using aromatase inhibitors in the treatment of males and females during controlled mating programs.

There is also substantial clinical evidence to indicate that many tumor types are associated with elevated estrogen production. Ovariectomy, adrenalectomy and hypophysectomy are commonly employed in patients with breast cancer as a means of reducing the amount of estrogen. Non-surgical procedures include treatments with high levels of steroids, anti-estrogens and inhibitors of steroidal enzymatic pathways. Treatment with antiestrogens results in about one-third of the patients obtaining objective tumor regressions. Andrenalectomy will cause regression of breast cancer in postmenopausal women with hormonal-dependent tumors, presumably as the result of reduction in available estrogen

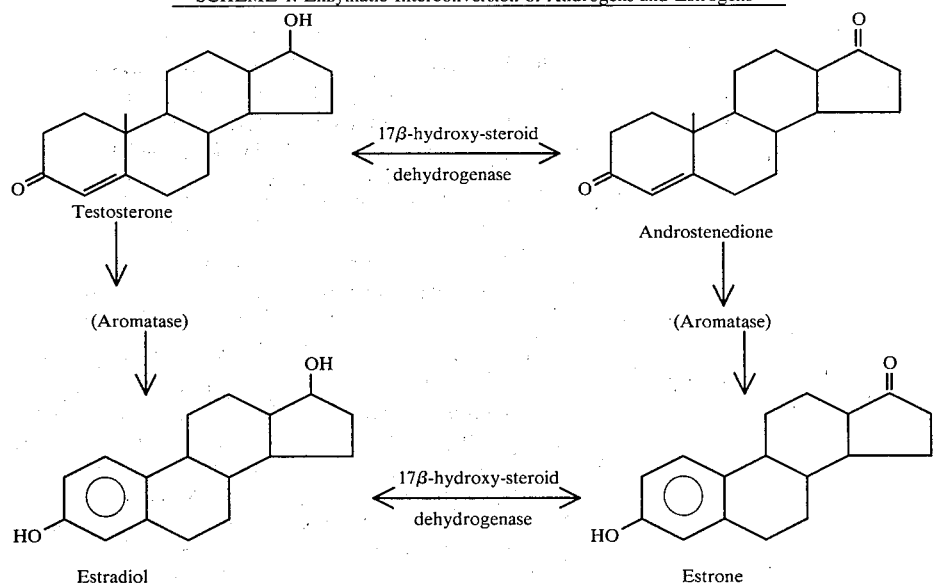

SCHEME 1. Enzymatic Interconversion of Androgens and Estrogens

Testosterone

Androstenedione (Aromatase)

(Aromatase)

Estradiol

Estrone

The conditions being treated with aromatase inhibitors can involve elevated levels of estrogens which are essentially steady or which may only be temporary surges resulting from cyclical body functions. Thus, aromatase inhibitors have been used for treatment of hyperestrogenemia in conditions such as gynecomastia and clinical improvement has resulted. They have also been used succesfully in treating male infertility associderived from androstenedione, whose source is primarily from the adrenals. Growth of several lines of breast cancer cells have been shown to be estrogen-dependent, and can be inhibited by compounds which antagonize estrogen action.

Thus, aromatase, inhibitors such as those named earlier, can effectively prevent the biologically active estrogens from reaching endrocrine tumors or reduce estrogen biosynthesis in those tumors capable of endogenous estrogen synthesis, thereby producing remissions of metastatic breast cancer.

Endometrial cancer has been related to the presence of excessive endogenous or exogenous estrogen. Gonadal and trophoblastic tumors cause somatic hyperestrogenization, which results in varying degrees of feminization in males. In females, the symptoms depend upon the age of the patient, and may range from precocious pseudopuberty to abnormalities of menses to post-menopausal bleeding. Aromatase inhibitors can be used in adjunctive therapy in the conservative management of patients with such tumors, since they will reduce the somatic expression of increased estrogen biosynthesis.

SUMMARY OF THE INVENTION

The present invention relates to 10-(2-alkynyl)-steroids. That is, it relates to steroids having a 2-alkynyl group at the 10-position in place of the angular methyl group. The compounds could also be considered as 19-(1-alkynyl)steroids in that the angular methyl group at the 10-position is further substituted by a 1-alkynyl group.

More specifically, the present invention relates to 10-(2-alkynyl)steroid aromatase inhibitors having the formula

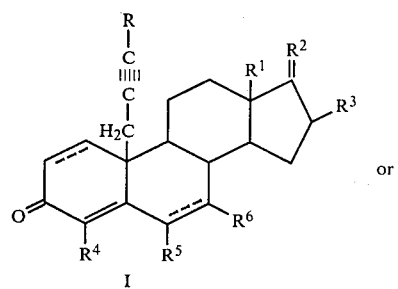

I

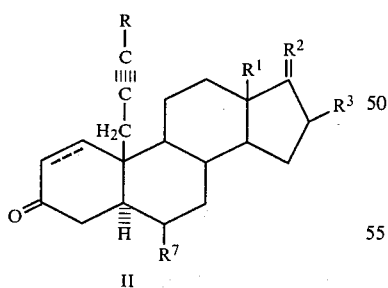

II wherein ═══ represents a single or a double bond; R is hydrogen or $C_{1-4}$ alkyl; $R^1$ is methyl or ethyl; $R^2$ is (H)($OR^8$) or ═O; $R^3$ is H or $C_{1-3}$ alkyl; $R^4$ is H or $OR^8$; $R^5$ is H, $C_{1-3}$ alkyl or, when the 5,6-bond is saturated, $R^5$ can be divalent ═O; $R^6$ and $R^7$ are each H or $C_{1-3}$ alkyl; and $R^8$ is H or $C_{2-4}$ alkanoyl.

The invention further includes novel intermediates useful for the preparation of the aromatase inhibitors, and having the formulae

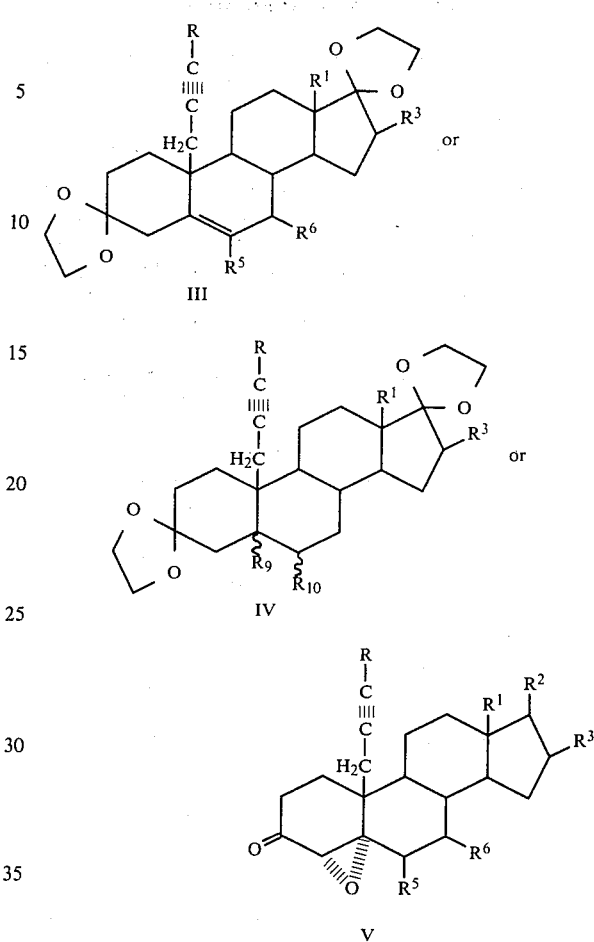

wherein R is hydrogen or $C_{1-4}$ alkyl, $R^1$ is $CH_3$ or $C_2H_5$, $R^2$ is (H)($OR^8$) or ═O; $R^3$ is H or $C_{1-3}$ alkyl; $R^5$ is H or $C_{1-3}$ alkyl; $R^6$ is H or $C_{1-3}$ alkyl; $R^8$ is H or $C_{2-4}$ alkanoyl; and $R^9$ and $R^{10}$ are each OH or $R^9$ and $R^{10}$ together are >O.

Methods of preparing and using the compounds of the invention are also included within the scope of the invention.

DETAILED DESCRIPTION OF THE INVENTION

In the compounds of Formulas I and II, R is hydrogen or $C_{1-4}$ alkyl such as methyl, ethyl, propyl or butyl and is preferably hydrogen; $R^1$ is methyl or ethyl but it is preferably methyl; $R^2$ is oxo, (H) (hydroxy) or (H) ($C_{2-4}$ alkanoyloxy) with the hydroxy or alkanoyloxy groups preferably having the β-configuration; $R^3$ is hydrogen or $C_{1-3}$ alkyl such as methyl, ethyl or propyl although hydrogen is preferred; $R_4$ is hydrogen, hydroxy or $C_{1-4}$ alkanoyloxy with hydrogen being preferred; $R^5$ is hydrogen, $C_{1-3}$ alkyl such as methyl, ethyl or propyl, or, when the 5,6-bond is saturated, $R^5$ is divalent and can be oxo; $R^6$ and $R^7$ are each hydrogen or $C_{1-3}$ alkyl such as methyl, ethyl or propyl although hydrogen is preferred for both; $R^8$ is hydrogen or $C_{2-4}$ alkanoyl such as acetyl, propionyl or butyryl with hydrogen preferred for $R^8$ and acetyl preferred when $R^8$ is alkanoyl. The compounds either have a 4,5-double bond, as shown in Formula I, or a 5α-hydrogen, as shown in Formula II. The compounds of formula I can additionally have a 1,2-double bond and/or a 6,7-double bond; the compounds of Formula II can also have a 1,2-double bond. Preferred are the compounds of Formula I having only a 4,5-double bond.

The compounds according to the invention are optically active and the stereochemistry at the ring junctions is the same as in the natural androstane series. Thus, the configuration of the alkynyl group is β, as are the angular hydrogen at C-8 and the angular substituent at C-13. In the compounds of Formulae I and II, the B/C and C/D ring junctions are trans, and the A/B ring junction is also trans in the compounds of Formula II. While the compounds having the natural steroid configuration as described are the active inhibitors, mixtures of those compounds with their optical antipodes are also included within the scope of the invention.

Specific and representative compounds according to the invention, in addition to those shown in the examples below, include but are not limited to the following:

7α-Methyl-10-(2-propynyl)estr-4-ene-3,17-dione

6α, 18-Dimethyl-10-(2-propynyl)-estra-1,4-diene-3,17-dione 4,17-Dihydroxy-16β-methyl-10-(2-propynyl)estra-4,6-dien-3-one 10-(2-Propynyl)estra-1,4-diene-3,6,17-trione 17β-Acetoxy-6β,16α-dimethyl-10-(2-propynyl)5α-estran-3-one 18-Methyl-10-(2-propynyl)5α-estr-1-ene-3,17-dione 17β-Hydroxy-10-(2-propynyl)estra-1,4-dien-3-one 4-Acetoxy-17β-hydroxy-10-(2-propynyl)estr-4-en-3-one 10-(2-Butynyl)estr-4-ene-3,17-dione.

The series of reactions used to prepare the various compounds of the present invention are illustrated in Scheme 2.

SCHEME 2

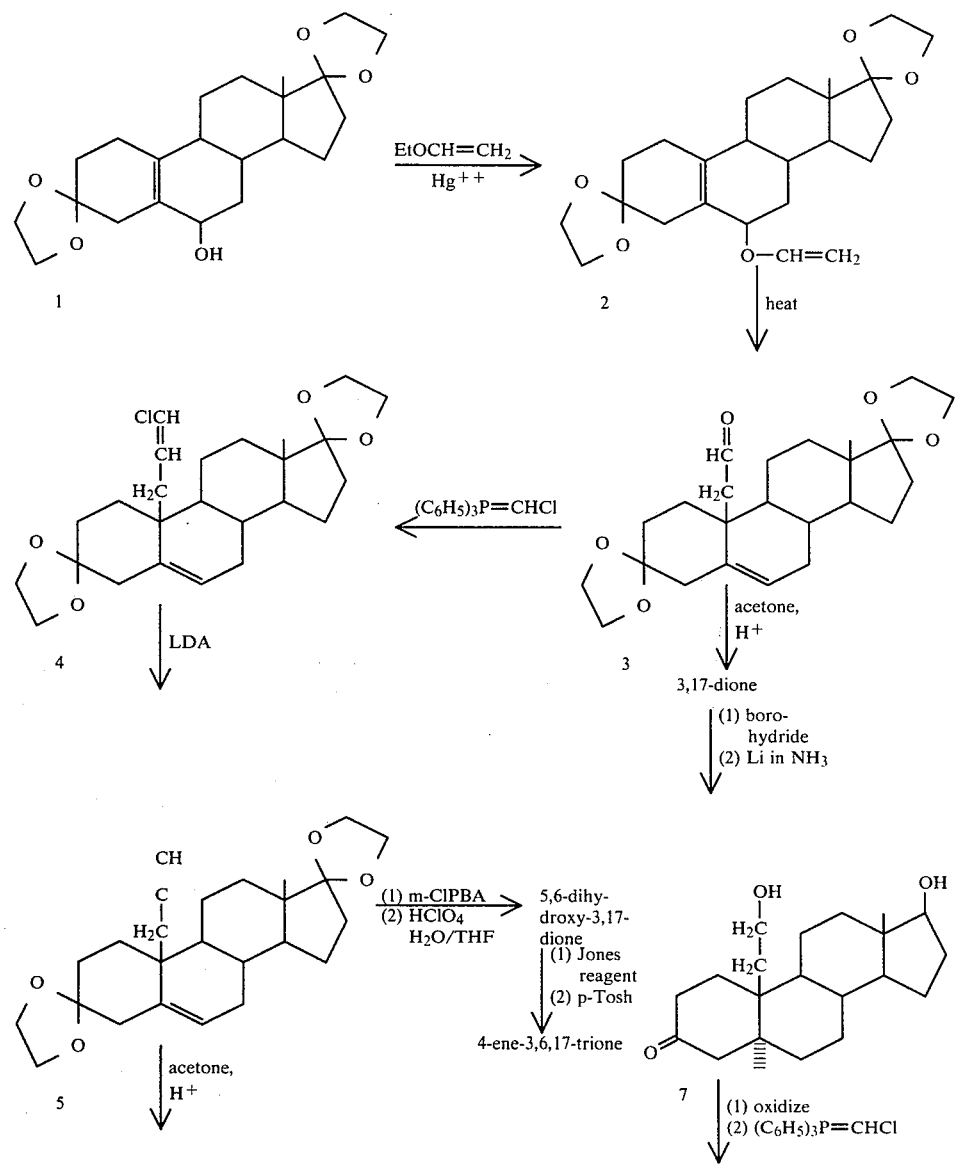

SCHEME 2 -continued

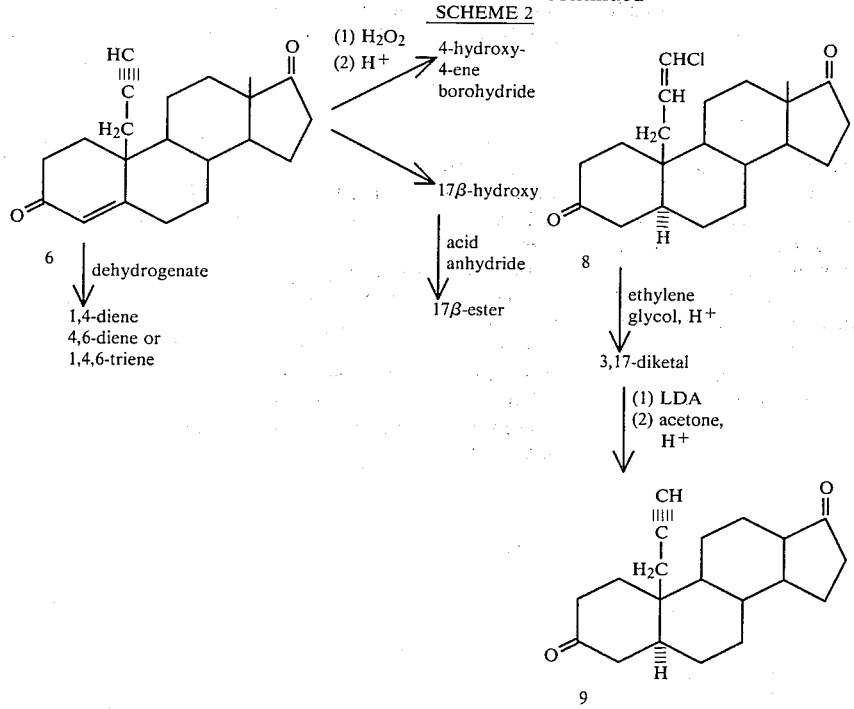

Thus, the known compound, a cyclic bis(ethylene acetal) of 6β-hydroxyestr-5(10)-en-3,17-dione (1) is reacted with an alkyl vinyl ether, in which the alkyl group contains 1 to 4 carbon atoms and is preferably ethyl, in the presence of a mercuric salt such as mercuric acetate to give the corresponding 6-vinyl ether (6β-vinyloxy compound)(2). This vinyl ether rearranges on heating to give the 19-carboxaldehyde (3) which is reacted with an appropriate chlorosubstituted ylide in a Wittig reaction to give the corresponding 19-(2-chloro-1-alkenyl)-steroid (4). More specifically, the aldehyde is reacted with a phosphorane made from (chloromethyl) triphenylphosphonium chloride or diphenyl chloromethylphosphonate and a strong base such as lithium diisopropylamide in an inert solvent such as tetrahydrofuran to give the 19-(2-chloro-1-ethenyl)steroid. The chloro compound obtained is usually a mixture of cis- and trans-isomers which is usually not separated but is used directly in the next step. The chloro compound is dehydrohalogenated using a strong base such as lithium diisopropylamide, potassium t-butoxide or sodamide to give the alkynyl compound (5). The protecting groups ]cyclic bis(ethylene acetal) groups] are then removed by reaction of the compound with acetone or butanone in the presence of a catalytic amount of acid such a p-toluenesulfonic acid or in alcohol containing mineral acid give the desired 10β-(2-propynyl) compound (6).

While this compound is itself a useful and active compound of the present invention, it can also serve as a very useful intermediate for the preparation of other related compounds. Thus, the 17-ketone can be reduced, for example, with a borohydride reducing agent such as potassium borohydride, to give the corresponding 17β-hydroxy compound which can be further reacted with an alkanoic acid or anhydride, each containing up to 4 carbon atoms, to give the corresponding 17-ester.

The 10β-(2-propynyl)estr-4-ene-3,17-dione (6) can also be treated with a variety of dehydrogenating agents to introduce further unsaturation into the compounds. Thus, treatment with dichlorodicyanoquinone gives the 1,4-diene while treatment with chloranil in tert-butanol gives the 4,6-diene and treatment of this diene with dichlorodicyanoquinone gives the 1,4,6-triene. In addition, the ketal (5) can be treated with the methyllithium and then methyl bromide to give the corresponding butynyl ketal and the protecting groups are removed as described earlier to give the 10-(2-butynyl) compound corresponding to (6).

On the other hand, to obtain the compounds in which the steroid is saturated, it is necessary to use the 19-carboxaldehyde (3) obtained earlier. The protecting groups at the 3- and 17-positions are removed by treatment with acetone or 2-butanone in the presence of an acid such as p-toluenesulfonic acid. This give the Δ⁴-3,17-diketone which is treated with a reducing agent, preferably a borohydride such as sodium borohydride, to reduce the 17-ketone and the 19-carboxaldehyde to the corresponding alcohols. The compound is then further treated with lithium in ammonia to reduce the unsaturation at the 4-position (7) and the two alcohols are oxidized back to the carbonyl groups by reaction with pyridinium chlorochromate.

As with the aldehyde obtained earlier, this aldehyde is reacted with an appropriate chloro-substituted ylide in a Wittig reaction to give the corresponding 19-(2-chloro-1-alkenyl)steroid (8). More specifically, the aldehyde is reacted with a phosphorane made from (chloromethyl)triphenylphosphonium chloride and a strong base such as lithium diisopropylamide in an inert solvent such as tetrahydrofuran to give the 19-(2-chloro-1-ethenyl)steroid. To avoid reaction with any of the other ketone groups present elsewhere in the molecule, only one equivalent of the triphenylphosphonium chloride is used. The chloro compound is usually obtained as a mixture of cis- and trans-isomers which is usually not separated but is used directly in the next step. In this case, protecting groups are reintroduced at the 3- and 17-positions by reacting the diketone with ethylene glycol in the presence of an acid such a p-toluenesulfonic acid. The chloro compound is then dehydrohalogenated and the protecting groups are removed in the same manner as described earlier to give 10β-(2-propynyl)-5α-estra-3,17-dione. This compound can be further dehydrogenated, for example, with dichlorodicyanoquinone, to give the corresponding Δ'-compound, 10β-(2-propynyl)-5α-estr-1-ene-3,17-dione.

Other compounds oxygenated at the 4- or 6-position can be prepared from materials described earlier. Thus, reaction of 10β-(2-propynyl)estr-4-ene-3,17-dione (6) with alkaline hydrogen peroxide gives the 4,5-epoxide. Treatment of the epoxide with acetic acid and a trace of sulfuric acid gives the corresponding 4-hydroxyestr-4-ene. On the other hand, reaction of the cyclic bis(ethylene acetal) of 10β-(2-propynyl)estr-5-ene-3,17-dione (5) with m-chloroperbenzoic acid gives the corresponding 5α,6α-epoxide which is then hydrolyzed (e.g., in the presence of perchloric acid) to give the corresponding 5α,6β-diol. When the hydrolysis is carried out in the presence of acid, the protecting groups at the 3- and 17-positions are also removed by the reaction. Treatment of the diol with an oxidizing agent such as Jones reagent gives the corresponding 5α-hydroxy-6-ketone. This is then readily dehydrated, for example by using p-toluenesulfonic acid in benzene, to give the desired 10-(2-propynyl)estr-4-ene-3,6,17-trione.

The cyclic bis(ethylene acetal) of 6β-hydroxy-estr-5(10)-ene-3,17-dione (1) used as the starting material above is a known compound and is obtained by the alkaline hydrolysis of the corresponding 6β-acetoxy compound. That compound is in turn obtained from the cyclic bis(ethylene acetal) of 19-hydroxyestr-5-ene-3,17-dione by treatment with lead tetraacetate. This same series of reactions can also be used for the conversion of other appropriately substituted compounds to the corresponding 6β-hydroxy compounds which would then be used in further reactions as described above.

To obtain compounds alkylated at C-16, 10-(2-propynyl)-estr-4-ene-3,17-dione is reduced to the 17β-hydroxy compound using borohydride and the 3-ketone is converted to the ketal using ethylene glycol and p-toluenesulfonic acid in refluxing benzene. The resulting compound is then further reacted with trimethylsilyl chloride to give the corresponding 10-(3-trimethylsilyl-2-propynyl) compound. Oxidation of the 17-alcohol with chromium trioxide/pyridine complex in dichloromethane, according to the procedure of Ratcliffe et al., *J. Org. Chem.*, 35, 4000 (1970), regenerates the 17-ketone which can be monoalkylated at C-16 by, e.g., reaction with methyl chloroformate and potassium t-butoxide, followed by an appropriate lower alkyl halide to give a 16-alkyl-16-methoxycarbonyl steroid. Alkaline hydrolysis followed by acidification and warming achieves decarboxylation, deketalization and removal of the trimethylsilyl group to give the desired 16-alkyl-10-(2-propynyl)estr-4-ene-3,17-dione.

Alkylation at C₆ can be effected using the 5,6-epoxide referred to earlier. This is reacted with an excess of the appropriate lower alkyl Grignard reagent in refluxing tetrahydrofuran to give the corresponding 6β-alkyl-5α-hydroxy compound. The acetal protecting groups are removed by mineral acid and dehydration of the alcohol is carried out by treatment with acid such as p-toluenesulfonic acid in benzene. This gives the desired 6β-alkyl-4-ene-3,17-dione.

Compounds containing a 7-alkyl substituent can be obtained from the 4-ene-3,17-dione (6) described earlier. Following procedures discussed earlier for the same or similar compounds, this is dehydrogenated to the 4,6-diene which is then reduced with a borohydride to give the 17β-hydroxy compound and the alcohol is esterified using acetic anhydride. The resulting compound, 17β-acetoxy-10-(2-propynyl)estr-4,6-dien-3-one, is then reacted with lithium di(lower alkyl) copper to give the 7α-alkyl-4-en-3-one. This compound can be further dehydrogenated as described for (6).

The 18-methyl series can be obtained from the known precursor (10) prepared according to the procedure of Baddely et al., *J. Org. Chem.*, 31, 1026 (1966). To obtain the 10-(2-propynyl) series, the hydroxyenone (10) is reacted as shown in Scheme 3.

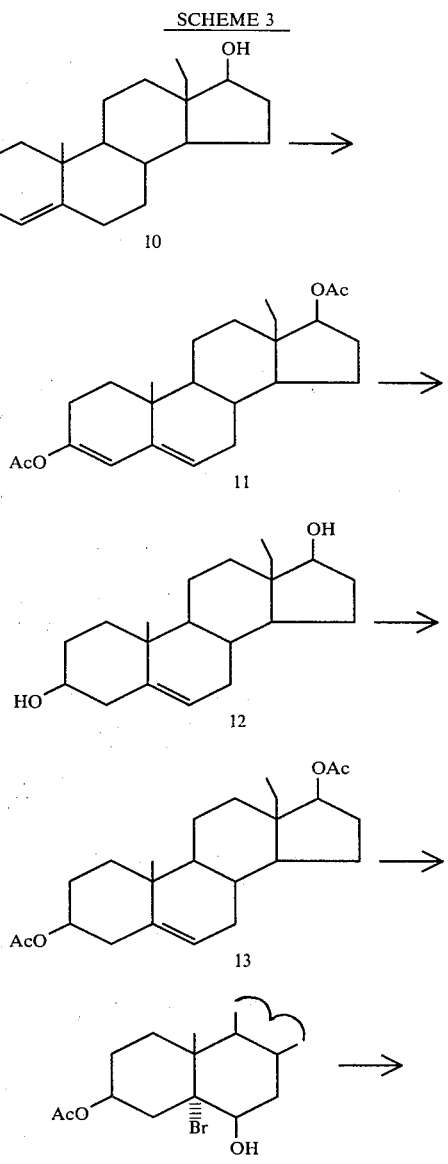

SCHEME 3

-continued
SCHEME 3

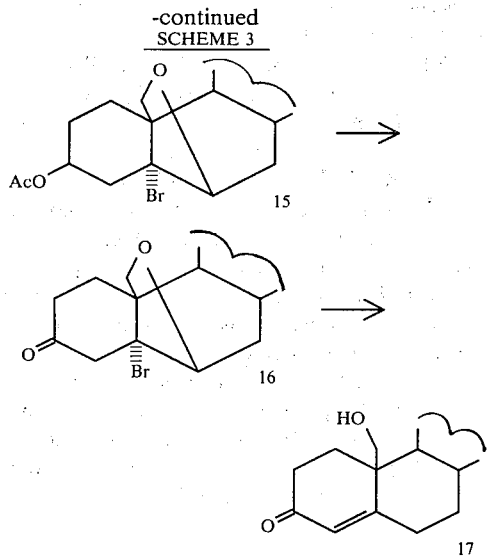

The known hydroxyenone (10) is converted to the enol diacetate (11) with isopropenyl acetate. Reduction with sodium borohydride, according to the procedure of Dauben et al., *J. Am. Chem. Soc.*, 73, 4463 (1951), produces enediol (12), which is converted to its diacetate (13) by conventional treatment with acetic anhydride and pyridine.

By analogy to the known compound with a methyl group at C-13, diacetate (13) is further elaborated using the procedure of Bowers et al., *J. Am. Chem. Soc.*, 84, 3204 (1962).

The diacetate (13) is converted to bromohydrin (14) with N-bromo-succinimide. Lead tetracetate treatment produces cyclic ether (15), which is converted to ketone (16) by hydrolysis of the acetate and oxidation. Treatment with metallic zinc effects a reductive opening of the ether and conjugation of the enone double bond, to produce the 4-ene-3-one-19-ol (17). The 19-alcohol (17) can be oxidized to the 6-hydroxy compound after ketalization at the 3- and 17-positions and transformed further by the procedures discussed earlier.

The foregoing syntheses are illustrative, and many other conventional reactions and combinations of these reactions may be used to produce or to interconvert the compounds of the invention. These conventional reactions and conditions may be found, e.g., in Fieser et al., "Steroids" (Reinhold, New York, 1959); Djerassi, Ed., "Steroid Reactions" (Holden-Day, San Francisco, 1963); Kirk et al., "Steroid Reaction Mechanisms" (Elsevier, Amsterdam, 1968); Carruthers, "Some Modern Methods of Organic Synthesis" (Cambridge U. Press, Cambridge, 1971); and Harrison et al., "Compendium of Organic Synthetic Methods" (Wiley-Interscience, New York, 1971).

The compounds of the present invention are inhibitors of aromatase and as such are useful in treating hyperestrogenemia. Thus, the compounds are useful in controlling (abnormally) high levels of estrogens both when the high levels observed are relatively steady or when they are brief surges occurring as part of cyclical body functions. Both females and males can be treated although, obviously, the absolute amount of estrogen which would be considered high in males would be much lower than the amount in females. Particularly preferred compounds are those in which the steroid nucleus contains only one double bond, located at the 4-position. Such $\Delta^4$-compounds are irreversible aromatase inhibitors in that there is irreversible binding with the aromatase enzyme.

The compounds are thus useful as anti-fertility agents to prevent ovulation or implantation in females or to reduce the mating behavior in males where brain aromatization is required for such behavior. The compounds would also have value in treating gynecomastia, male infertility resulting from elevated estrogen levels, and hyperestrogenemia which may precede myocardial infarction. The compounds may also have value in the treatment of breast cancer and various estrogen-induced or stimulated tumors. The aromatase inhibitory action of the compounds of the invention can be determined using a radioenzymatic assay. An aromatase enzyme preparation from the microsomal fraction isolated from human placenta is employed. Stereospecific elimination of $1\beta$ and $2\beta$ tritium labels from androgen substrates such as testosterone or androstenedione and the subsequent appearance of tritiated water is utilized to measure the rate of enzyme reaction during in vitro incubations.

The enzyme affinity of the present aromatase inhibitors is determined by measuring their competive inhibition of the conversion of $^3$H-testosterone to estrogens. The $1\beta$, $2\beta$-$^3$H-testosterone (40-60 Ci/mM specific activity) is dissolved in assay buffer to provide an assay concentration of about $1.7\times10^{-9}$ M with approximately 200,000 disintegrations per minute in 100 µl. Assay buffer contains 100 mM KCl, 10 mM KH$_2$PO$_4$, 10 mM dithiothreitol and 1 mM EDTA at pH 8.0. Inhibitor compounds (~10 mg) are dissolved in ethanol and/or dimethylsulfoxide and diluted with assay buffer to provide assay concentrations ranging from $10^{-4}$ M to $10^{-9}$ M. Tritium-labeled testosterone (substrate) 100 µl (~$2.6\times10^{-8}$ M), and enzyme inhibitor, 100 µl, are added to a 35 ml centrifuge tube containing 600 µl of a NADPH generating system. Aromatase requires NADPH as a cofactor, therefore a generating system is included which uses 0.5 mM NADP$^+$, 2.5 mM glucose-6-phosphate, and 1.0 unit/ml of glucose-6-phosphate dehydrogenase in assay buffer. The enzyme reaction is initiated by the addition of 700 µl of aromatase preparation, usually 50 µg microsomal protein per ml of assay buffer. These preparations are mixed using a vortex mixer and incubated for 30 minutes at 37° C. with 95% O$_2$:5% CO$_2$ gas phase in a Dubinoff shaking incubator.

The enzymatic reaction is terminated by the addition of CHCl$_3$. After vortexing 20 seconds, aqueous/organic emulsions are dispersed and phase separation achieved following centrifugation at 600×g for 10 minutes. Duplicate 500 µl samples of the upper aqueous phase of each incubation sample are added to 10×75 mm culture tubes. To these tubes, 500 µl of cold 0.25% dextran-coated charcoal suspension is added, vortexed, incubated for 15 minutes at 4° C., then centrifuged at 2600×g in a refrigerated centrifuge (4° C.). The supernatant fraction is decanted into a 20 ml scintillation vial and 15 ml of aqueous scintillation cocktail is added. The radioactivity of $^3$H$_2$O resulting from liberated $1\beta$ and $2\beta$ tritium atoms during the enzymatic reaction is determined by counting for 10 minutes in a liquid scintillation counter. This assay procedure is adapted from the procedures of Reed et al., *J. Biol. Chem.*, 251, 1625 (1976), and Thompson et al., *J. Biol. Chem.*, 249, 5364 and 5374 (1974).

The enzymatic activity is related to the percentage of tritium liberated from $^3$H-testosterone which appears as $^3$H$_2$O. The activity of each concentration of inhibitor is calculated as a percentage of the vehicle control, which is arbitrarily set at 100%. The molar concentration of each inhibitor which reduces enzyme activity by 50% is called the 50% Inhibition Concentration, IC$_{50}$. These values for an inhibitor of the invention, 10-(2-propynyl)estr-4-ene-3,17-dione, and the reference compounds aminoglutethimide, androsta-1,4,6-triene-3,17-dione and 1-dehydrotestololactone, are shown in Table 1. The 10-(2-propynyl) compound has greater enzyme affinity than other known inhibitors, which have been used either as antifertility agents in rodents or to block peripheral aromatization in patients with breast cancer.

TABLE 1

| Competitive Inhibition of Aromtase Inhibitors | |
|---|---|
| Inhibitor Compounds | IC$_{50}$ |
| 10-(2-propynyl)estr-4-ene 3,17-dione | $4.2 \times 10^{-9}$M |
| α-(p-Aminophenyl-α-ethylglutarimide (aminoglutethimide) | $1.0 \times 10^{-6}$ |
| Androsta-1,4,6-triene-3,17-dione | $1.0 \times 10^{-7}$ |
| 1,2,3,4,4a,7,9,10,10a-Decahydro-2-hydroxy-2,4b-dimethyl-7-oxo-1-phenanthrene-propionic acid 0-lactone | $2.5 \times 10^{-6}$ |

The compounds of the invention, which demonstrate good inhibition, IC$_{50}$ ≦ $10^{-7}$ M, were evaluated for time-dependent inhibition. In this assay, the inhibitor is preincubated with enzyme prior to assaying for enzyme activity in the presence of high substrate levels. A time-related decrease in enzyme activity is indicative of irreversible binding of the inhibitor with the enzyme.

In the time-dependent assay, an amount of the enzyme inhibitor in 100 μl of the assay buffer described above which will provide assay concentrations which are approximately one and ten times the IC$_{50}$ values are added to 35 ml centrifuge tubes containing 600 μl of the NADPH generating system described above. The preincubation is started by the addition of 700 μl of aromatase preparation, usually 500–800 μg of microsomal protein per ml of assay buffer. These preparations are mixed using a vortex mixer and incubated for 0, 10, 20 or 40 minutes at 25° C. Then 100 μl of testosterone ($\sim 6.8 \times 10^{-6}$ M) spiked with 1β,2β-$^3$H testosterone is added in assay buffer to provide an assay concentration of substrate ($4.5 \times 10^{-7}$M) which is at least ten times the Km of testosterone (0.045 μM). Following vortexing, the enzyme incubation is continued for 10 minutes before being terminated by the addition of chloroform. The amount of radioactivity in the aqueous fraction is determined by scintillation procedures. The enzymatic activity is calculated from the percent of $^3$H-testosterone converted to $^3$H$_2$O. The enzyme activity for each concentration of inhibitor at each time period of preincubation is calculated as a percent of the "0" minute vehicle control arbitrarily set at 100%. Therefore, the present enzyme inhibition is expressed as a percentage: [100 percent minus percent enzyme activity of inhibitor].

Compounds which show time-dependent inhibition are then assayed to establish the inhibition constant, K$_i$, which is the apparent dissociation constant for the enzyme-inhibitor complex. This determination requires measurements at initial velocities of enzyme reaction. The enzyme activity is determined following different preincubation times at various inhibitor concentrations when assayed at a substrate concentration of at least ten times the Km of testosterone. The enzyme half-life (t$_\frac{1}{2}$) at these different inhibitor concentrations ([In]) is used to determine the K$_i$ by the linear regression equation of the t$_\frac{1}{2}$ vs. 1/[In]. The K$_i$ is equivalent to the inhibitor concentration when t$_\frac{1}{2}$ is equal to zero.

The apparent K$_i$ for the 10-(2-propynyl)estr-4-ene-3,17-dione is $8.9 \times 10^{-9}$ M. These data indicate that this inhibitor is irreversibly bound to the enzyme with an affinity for the enzyme site which is five times greater than that of the natural substrate testosterone, which has an enzyme affinity (Km) of $4.5 \times 10^{-8}$ M.

These data demonstrate that 10-(2-propynyl)estr-4-ene-3,17-dione is superior to known aromatase inhibitors. Significant irreversible aromatase inhibition is also shown by the other compounds of the invention of Formulae I and II.

In the treatment of hyperestrogenemia, the compounds of the invention may be administered in various manners to the patient being treated to achieve the desired effect. As used herein in the treatment of hyperestrogenemia, the term patient is taken to mean warm blooded animals, such as rats, dogs and humans. The compounds can be administered alone or in combination with one another. Also, the compounds can be administered in the form of a pharmaceutical preparation. The compounds may be administered orally, parenterally, for example, intravenously, intraperitoneally, intramuscularly or subcutaneously, including injection of the active ingredient directly into tissue or tumor sites such as the mammary gland. The amount of compound administered will vary over a wide range and can be any effective amount. Depending on the patient to be treated, the condition being treated and the mode of administration, the effective amount of compound administered will vary from about 1 to 250 mg/kg of body weight per day and preferably from 10 to 50 mg/kg of body weight per day. Unit dosages for oral or parenteral administration may contain, for example, from 10 to 150 mg of a compound of the invention.

For parenteral administration the compounds may be administered as injectable dosages of a solution of suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as propylene glycol or polyethylene glycol are preferred liquid carriers, particularly for injectable solutions.

The compounds can be administered in the form of a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation.

The following are illustrative pharmaceutical formulations suitable for oral or parenteral administration which may be employed in practicing the present invention:

| TABLET | |
|---|---|
| (a) 10β-(2-propynyl)estr-4-ene-3,17-dione | 75 g |
| (b) Lactose | 1.216 Kg |
| (c) Corn starch | 0.3 Kg |

Mix the active ingredient, the lactose and corn starch uniformly. Granulate with 10% starch paste. Dry to a moisture content of about 2.5%. Screen through a No. 12 mesh screen. Add and mix the following:

| | |
|---|---|
| (a) Magnesium Stearate | 0.015 Kg |
| (b) Corn starch qs ad | 1.725 Kg |

Compress on a suitable tablet machine to a weight of 0.115 g/tablet.

| SOFT GELATINE CAPSULE | |
|---|---|
| (a) 10β-(2-propynyl)estr-4-ene-3,17-dione | 0.25 Kg |
| (b) Polysorbate 80 | 0.25 Kg |
| (c) Corn oil qs ad | 25.0 Kg |

Mix and fill into 50,000 soft gelatin capsules.

| IM DEPOT INJECTION | |
|---|---|

Each 1 ml contains the following:

| | |
|---|---|
| (a) 10β-(2-propynyl)estr-4-ene-3,17-dione | 5.0 mg |
| (b) Anhydrous chlorobutanol | 5.0 mg |
| (c) Aluminum monostearate | 50.0 mg |
| (d) Peanut oil qs ad | 1.0 ml |

Dissolve or disperse the ingredients in the peanut oil.

| DEPOT-IMPLANT | |
|---|---|
| (a) 10β-(2-propynyl)estr-4-ene-3,17-dione | 5.0 mg |
| (b) Dipmethylsiloxane | 240.0 mg |
| (c) Catalyst qs | |

Disperse the drug substance in the fluid dimethylsiloxane. Add the catalyst and case into a suitable monolytic structure.

Alternatively, the drug substance may be enclosed by a precast, polydimethylsiloxane envelope.

Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate moldable gel (Hydron).

| IM INJECTIONS | |
|---|---|
| A. Oil type: | |
| (a) 10β-(2-propynyl)estr-4-ene-3,17-dione | 25.0 mg |
| (b) BHA, BHT aa | 0.01% w/v |
| (c) Peanut oil or sesame oil qs | 1.0 ml |
| B. Suspension type: | |
| (a) 10β-(2-propynyl)estr-4-ene-3,17-dione | 25.0 mg |
| (b) Sodium carboxymethylcellulose | 0.5% w/v |
| (c) Sodium bisulfite | 0.02% w/v |
| (d) Water for injection, qs | 1.0 ml |
| BUCCAL OR SUBLINGUAL TABLET | |
| (a) 10β-(2-propynyl)estr-4-ene-3,17-dione | 1% |
| (b) Calcium stearate | 1% |
| (c) Calcium sacchrin | 0.02% |
| (d) Granular mannitol | qs |

Mix and compress on a suitable tablet machine to a weight of 0.115 g/tablet.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 30 ml of freshly distilled ethyl vinyl ether, 2.1 g of 3,3,17-17-bis(ethylenedioxy)estr-5(10)-en-6β-ol and 800 mg of mercuric acetate is refluxed for 2 hours and then 250 mg of fresh mercuric acetate is added. Heating is resumed for an additional 2 hours followed by the addition of 250 mg of fresh mercuric acetate, refluxing for 2 hours, addition of 250 mg of mercuric acetate, and, finally, heating at reflux for 16 hours. Aqueous sodium carbonate solution is added to the cooled mixture which is stirred for 15 minutes before it is diluted with ether. The organic layer is separated, washed with aqueous sodium chloride solution and dried and the solvent is evaporated. The residue obtained is purified by flash chromatography on silica gel and 40% ethyl acetate-hexane to give 3,3,17,17-bis-(ethylenedioxy)-6β-vinyloxyestr-5(10)-ene melting at about 82°–83° C. after recrystallization from hexane.

A solution of 950 mg of 3,3,17,17-bis(ethylenedioxy)6β-vinyloxyestr-5(10)-ene in 20 ml of sym-collidine is heated at 170°–175° C. for 3 hours. The solvent is then removed by distillation under reduced pressure and the resulting residue is purified by flash chromatography on silica gel in 40% ethyl acetate-hexane to give 3,3,17,17-bis(ethylenedioxy)androst-5-ene-19-carboxaldehyde melting at about 128°–130° C. after recrystallization from ethyl acetate-pentane.

A solution of lithium diisopropylamide, prepared from 0.26 ml of diisopropylamine and 0.85 ml of a 2.1 molar solution of butyllithium, all in 5 ml of tetrahydrofuran, is added to 640 mg of (chloromethyl)triphenylphosphonium chloride in 5 ml of tetrahydrofuran at −70° C. The mixture is kept at −70° C. for 10 minutes, 560 mg of 3,3,17,17-bis(ethylenedioxy)androst-5-ene-19-carboxaldehyde in 4 ml of tetrahydrofuran is added, and the mixture is allowed to warm to room temperature. It is then poured into water and the resulting mixture is extracted with ether. The ether is evaporated and the residue, a mixture of isomers (cis and trans) of 3,3,17,17-bis(ethylenedioxy)-10-(3-chloroprop-2-enyl)-estr-5-ene, is isolated by flash chromatography on silica gel in 40% ethyl acetate-hexane.

The chloro compound obtained in the preceding paragraph is dissolved in 2 ml of tetrahydrofuran and added to lithium diisopropylamide prepared from 0.18 ml of diisopropylamine, 0.6 ml of a 2.1 M solution of butyllithium, and 3 ml of tetrahydrofuran at −70° C. After 1.5 hours at −70° C., aqueous ammonium chloride solution is added, and the mixture is extracted with ether. The ether solution is dried and the solvent is evaporated to leave 3,3,17,17-bis(ethylenedioxy)-10-(2-propynyl)estr-5-ene as a crystalline residue which is used directly in the next step. (The compound melts at 152°–153° C. after recrystallization from ethyl acetate-pentane.) The crystalline residue is treated with 30 ml of acetone containing 20 mg of p-toluenesulfonic acid and it is allowed to stand at room temperature for 16 hours. The solvent is then evaporated and the residue is purified by flash chromatography on silica gel in 50% ethyl acetate-hexane, followed by recrystallization from ethyl acetate-hexane, to give 10-(2-propynyl)estr-4-ene-3,17- dione melting at about 174°–175° C. This compound has the following structural formula

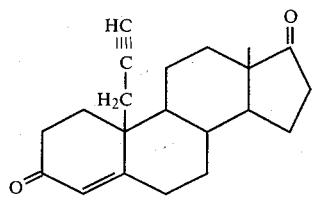

EXAMPLE 2

A mixture of 60 mg of 3,3,17,17-bis(ethylenedioxy)androst-5-ene-19-carboxaldehyde and 15 mg of p-toluenesulfonic acid in 30 ml of acetone is stirred for 16 hours at room temperature and then concentrated to dryness. The residue is dissolved in ether and the ether solution is washed with aqueous sodium bicarbonate and dried and the solvent is evaporated to give 3,17-dioxoandrost-4-ene-19-carboxaldehyde. This is treated with 18 mg of sodium borohydride in 10 ml of methanol at 0° C. for 1 hour. Acetic acid (0.05 ml) is then added and the mixture is evaporated to dryness. The residue is dissolved in ether, the ether solution is washed with 1 normal hydrochloric acid solution and then dried and the solvent is evaporated to leave a residue which is 17β-hydroxy-10-(2-hydroxyethyl)estr-4-en-3-one.

A solution of 300 mg of 17β-hydroxy-10-(2-hydroxyethyl)estr-4-en-3-one in 500 ml of tetrahydrofuran is added to 30 mg of lithium in liquid ammonia at reflux. After 15 minutes at this temperature, solid ammonium chloride is added and the ammonia is allowed to evaporate. The residue is dissolved in ether, the ether solution is washed with aqueous sodium chloride and then dried, and the solvent is evaporated to give, as a residue, 17β-hydroxy-10-(2-hydroxyethyl)-5α-estran-3-one. To a solution of 500 mg of this product in methylene chloride, there is added 650 mg of pyridinium chlorochromate and the mixture is stirred at 25° C. for 16 hours. Ether is then added and the mixture is filtered. The filtrate is washed with 1 N hydrochloric acid, aqueous sodium bicarbonate and brine and dried, and the solvent is evaporated to give, as a residue, 3,17-dioxo-5α-androstane-19-carboxaldehyde.

A solution of lithium diisopropylamide, prepared from 0.26 ml of diisopropylamine and 0.85 ml of a 2.1 M solution of butyllithium and 5 ml of tetrahydrofuran is added to a solution of 640 mg of (chloromethyl)triphenylphosphonium chloride in 5 ml of tetrahydrofuran at −70° C. After 10 minutes at −70° C., a solution of 560 mg of 3,17-dioxo-5α-androstane-19-carboxaldehyde in 4 ml of tetrahydrofuran is added and the mixture is allowed to warm to room temperature. The mixture is then poured into water and extracted with ether. The solvent is evaporated and the residue is purified by flash chromatography on silica gel in 50% ethyl acetate-hexane to give 10-(3-chloroprop-2-enyl)-5α-estrane-3,17-dione as a mixture of isomers.

The product obtained in the preceding paragraph is dissolved in 20 ml of benzene containing 4 ml of ethyleneglycol and 30 mg of p-toluenesulfonic acid. The mixture is refluxed for 16 hours with the removal of any water that is formed. Ether is added to the cooled mixture which is washed with water, aqueous sodium bicarbonate and brine, and dried, and the solvent is evaporated to give 3,3,17,17-bis(ethylenedioxy)-10-(3-chloroprop-2-enyl)-5α-estrane which is purified by flash chromatography on silica gel in 50% ethyl acetate-hexane.

A solution of 243 mg of 3,3,17,17-bis(ethylenedioxy)-10-(3-chloroprop-2-enyl)-5α-estrane in 2 ml of tetrahydrofuran is added to lithium diisopropylamide prepared from 0.18 ml of diisopropylamine and 0.6 ml of a 2.1 M solution of butyllithium and 3 ml of tetrahydrofuran at −70° C. After 1.5 hours at −70° C., aqueous ammonium chloride is added, and the mixture is extracted with ether. The ether extract is dried and concentrated to leave a residual crystalline product which is 3,3,17,17-bis(ethylenedioxy)-10-(2-propynyl)-5α-estrane. This product is treated with 30 ml of acetone containing 10 mg of p-toluenesulfonic acid at room temperature for 16 hours and the solvent is then evaporated. The residue is purified by flash chromatography on silica gel in 50% ethyl acetate-hexane, followed by recrystallization from ethyl acetate-hexane to give 10-(2-propynyl)-5α-estrane-3,17-dione. This compound has the following structural formula

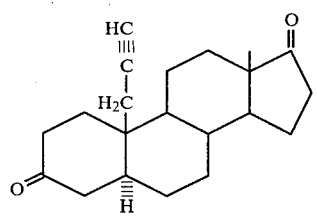

EXAMPLE 3

A solution of 312 mg of 10-(2-propynyl)estr-4-ene-3,17-dione in 10 ml of absolute methanol is treated with 15 mg of potassium borohydride at 0° C. for 1 hour. Acetic acid (0.05 ml) is added and the solvent is evaporated. The residue is dissolved in ether, the ether solution is washed with 1 N hydrochloric acid and with brine and dried, and the solvent is evaporated. The residue is recrystallized from methanol to give 17β-hydroxy-10-(2-propynyl)estr-4-en-3-one. This compound has the following structural formula

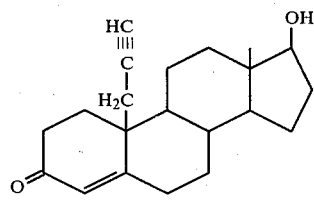

EXAMPLE 4

To a solution of 500 mg of 17β-hydroxy-10-(2-propynyl)estr-4-en-3-one in 4 ml of pyridine at 25° C. is added 4 ml of acetic anhydride and the mixture is allowed to stand at room temperature for 16 hours. It is then concentrated under reduced pressure, the residue is diluted with ether and the ether solution is washed with 1 N hydrochloric acid and with aqueous sodium bicarbonate and then dried and concentrated. The resultant residue is recrystallized from ethyl acetate-hexane to give 17β-acetoxy-10-(2-propynyl)estr-4-en-3-one. This compound has the following structural formula

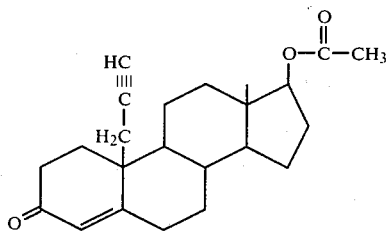

EXAMPLE 5

A mixture of 150 mg of 10-(2-propynyl)-estr-4-ene-3,17-dione, and 300 mg of dichlorodicyanoquinone in 10 ml of dioxane is refluxed for 20 hours. The mixture is cooled and diluted with ether and then washed with aqueous sodium carbonate and dried. The solvent is evaporated and the residue is chromatographed on silica gel in ethyl acetate/hexane to give 10-(2-propynyl)-estra-1,4-diene-3,17-dione melting at about 200°–201° C. This compound has the following structural formula

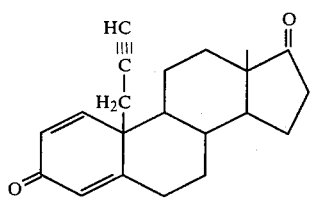

EXAMPLE 6

A mixture of 190 mg of 10-(2-propynyl)estra-4,6-diene-3,17-dione, 168 mg of dichlorodicyanoquinone and 10 ml of dioxane is heated at reflux for 5 hours. The mixture is cooled and filtered and the filtrate is diluted with ether, washed with aqueous 1 N sodium hydroxide solution and brine, dried and then concentrated. The resulting residue is chromatographed on silica gel using 50% ethyl acetate/hexane to give 10-(2-propynyl)estra-1,4,6-triene-3,17-dione. This compound melts at about 185°–189° C. after recrystallization from ethyl acetate/hexane and it has the following structural formula

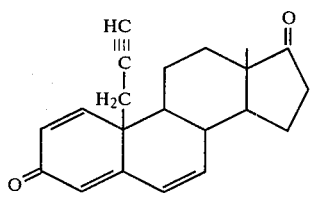

EXAMPLE 7

A mixture of 250 mg of 10-(2-propynyl)estr-4-ene-3,17-dione, and 460 mg of chloranil in 17 ml of tert-butyl alcohol is heated at reflux temperature for 3 hours. The mixture is diluted with ethyl acetate and filtered and the filtrate is washed with aqueous 1 N sodium hydroxide and with brine, and dried. The solvent is then evaporated and the residue is chromatographed on silica gel using ethyl acetate-hexane to give 10-(2-propynyl)estra-4,6-diene-3,17-dione. This compound has the following structural formula

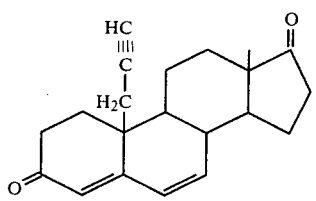

EXAMPLE 8

A mixture of 200 mg of 10-(2-propynyl)-5α-estra-3,17-dione and 320 mg of dichlorodicyanoquinone in 4 ml of dioxane is heated at reflux for 24 hours. The mixture is diluted with ethyl acetate and washed with aqueous 1 N solidum hydroxide and with brine, and then dried. The solvent is evaporated and the residue is chromatographed on silica gel using ethyl acetate-hexane to give 10-(2-propynyl)-5α-estr-1-ene-3,17-dione. This compound has the following structural formula

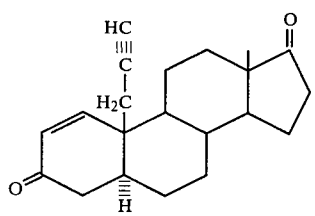

EXAMPLE 9

To a solution of 650 mg of 10-(2-propynyl)estr-4-ene-3,17-dione in 5 ml of methanol at 15° C. is added 0.6 ml of 30% hydrogen peroxide. A solution of 46 mg of sodium hydroxide in 0.4 ml of water is then added dropwise. After 1 hour at 15° C., the solution is stirred for 2 hours at 25° C. before it is poured into brine. The aqueous mixture is then extracted with ether and the ether solution is dried and concentrated. The residual material obtained is recrystallized from methanol to give 4,5β-epoxy-10-(2-propynyl)estrane-3,17-dione. This epoxide is added to 5 ml of acetic acid containing 0.1 ml of concentrated sulfuric acid and the mixture is stirred at 25° C. for 4 hours before it is poured into ice. The solid which forms is separated by filtration and recrystallized from ethyl acetate to give 4-hydroxy-10-(2-propynyl)estr-4-ene-3,17-dione. This compound has the following structural formula

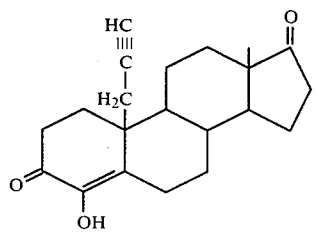

EXAMPLE 10

To a solution of 152 mg of 3,3,17,17-bis(ethylenedioxy)-10-(2-propynyl)estr-5-ene in 7 ml of dichloromethane is added 85 mg of 85% m-chloroperbenzoic acid. The mixture is maintained at 0° C. for 16 hours and then diluted with dichloromethane and washed with water, aqueous 10% sodium carbonate and brine before it is dried and the solvent is evaporated. The residue is subjected to flash chromatography on silica gel in 60% ethyl acetate-hexane to give 3,3,17,17-bis(ethylenedioxy)-5α,6α-epoxy-10-(2-propynyl)estrane. The corresponding 5β,6β-epoxy compound is also obtained.

A solution of 126 mg of the 5α,6α-epoxide in 20 ml of tetrahydrofuran and 5 ml of water is treated with 0.4 ml of 70% perchloric acid and stirred at 25° C. for 48 hours. At this point, thin layer chromatography showed the absence of epoxide. The resulting mixture is diluted with ether, washed with aqueous sodium carbonate solution and with brine, and then dried. Evaporation of the solvent then give crude 5α,6β-dihydroxy-10-(2-propynyl)estrane-3,17-dione.

The crude oil is dissolved in 25 ml of acetone at 0° C. and Jones reagent is added dropwise until a brown color persists for 15 minutes. The mixture is then extracted with dichloromethane and water. The organic layer is separated, washed with brine and dried, and the solvent is evaporated to give, as a residual oil, 5α-hydroxy-10-(2-propynyl)estrane-3,6,17-trione. This oil is dissolved in 50 ml of benzene, 15 mg of p-toluenesulfonic acid is added, and the mixture is refluxed for 30 minutes using a Dean-Stark trap. The mixture is then cooled, washed with aqueous sodium bicarbonate and with brine, and then dried. The solvent is evaporated to give, as a residue, 10-(2-propynyl)estr-4-ene-3,16,17-trione. This compound has the following structural formula

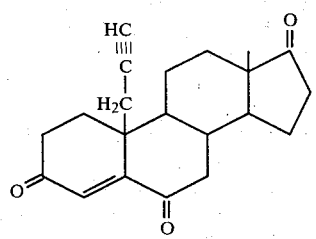

EXAMPLE 11

To a solution of 400 mg of 3,3,17,17-bis(ethylenedioxy)10-(2-propynyl)estr-5-ene in 5 ml of tetrahydrofuran at room temperature is added methyllithium (1.1 ml of a 1.0 M solution in ether). After 10 minutes, 200 mg of methyl iodide is added and the mixture is stirred at room temperature for about 8 hours. The mixture is then diluted with ether, washed with brine and dried and the solvent is evaporated to give a residue which is 10-(2-butynyl)-3,3,17,17-bis(ethylenedioxy)estr-5-ene. The ethylenedioxy groups are then removed by the procedure described in the last paragraph of Example 1 to give 10-(2-butynyl)estr-4-ene-3,17-dione.

The preceding examples can be repeated with similar success by substituting the generically or specifically prescribed reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound having the formula

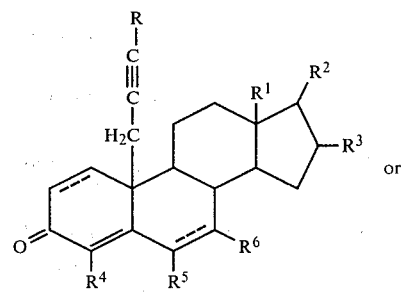

or

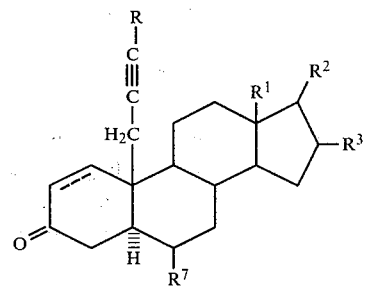

wherein === represents a single or a double bond; R is hydrogen or $C_{1-4}$ alkyl; $R^1$ is methyl or ethyl; $R^2$ is (H)($OR^8$) or =O; $R^3$ is H or $C_{1-3}$ alkyl; $R^4$ is H or $OR^8$; $R^5$ is H, $C_{1-3}$ alkyl or, when the 5,6-bond is saturated, $R^5$ can be divalent =O; $R^6$ and $R^7$ are each H or $C_{1-3}$ alkyl; and $R^8$ is H or $C_{2-4}$ alkanoyl.

2. The compounds of claim 1, wherein R is hydrogen.

3. The compounds of claim 1, wherein $R^1$ is methyl.

4. The compounds of claim 1, wherein $R^2$ is (H)(OH) or =O.

5. The compounds of claim 1 having formula I wherein $R^4$ is H or acetoxy.

6. The compounds of claim 1, wherein $R^3$ is H.

7. The compounds of claim 1 wherein === is a single bond.

8. The compounds of claim 1 having Formula I wherein $R^5$ is H.

9. The compounds according to claim 1 having the formula

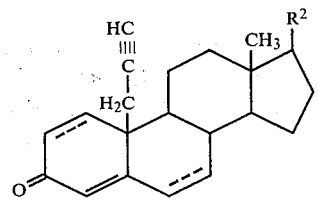

wherein === represents a single or double bond and $R^2$ is (H) (—OH) or =O.

10. 10-(2-Propynyl)estr-4-ene-3,17-dione, a compound of claim 1.

11. 17β-Hydroxy-10-(2-propynyl)estr-4-en-3-one, a compound of claim 1.

12. 10-(2-Propynyl)estra-1,4-diene-3,17-dione, a compound of claim 1.

13. 10-(2-Propynyl)estra-1,4,6-triene-3,17-dione, a compound of claim 1.

14. 4-Hydroxy-10-(2-propynyl)estr-4-en-3,17-dione, a compound of claim 1.

15. 6β-Hydroxy-10-(2-propynyl)estr-4-en-3,17-dione, a compound of claim 1.

16. 10-(2-Propynyl)estr-4-ene-3,6,17-trione, a compound of claim 1.

17. 10-(2-Propynyl)-5α-estra-3,17-dione, a compond of claim 1.

18. 10(2-Propynyl)-5α-estr-1-ene-3,17-dione, a compound of claim 1.

19. A method of inhibiting aromatase activity, which comprises contacting an aromatase enzyme with an effective inhibiting amount of a compound of claim 1.

20. A method of treating hyperestrogenemia which comprises administering to a subject having said condition a therapeutically effective aromatase inhibiting amount of a compound of claim 1.

21. A method according to claim 19 in which the aromatase inhibition produces an anti-fertility effect.

22. A process for the preparation of compounds of the formula

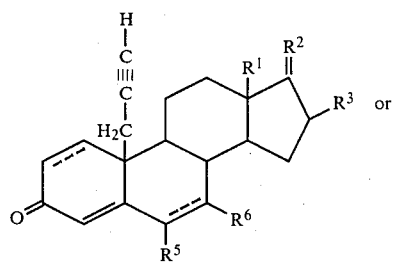

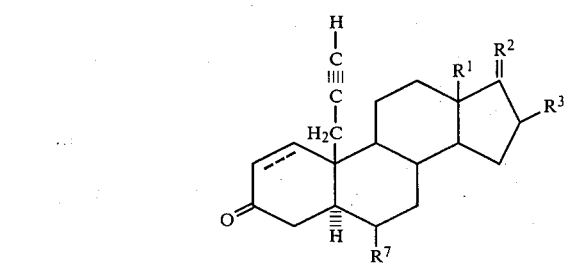

wherein === represents a single or a double bond; $R^1$ is methyl or ethyl; $R^2$ is (H)(OR$^8$) or =O; $R^3$ is H or $C_{1-3}$ alkyl; $R^5$ is H or $C_{1-3}$ alkyl; $R^6$ and $R^7$ are each H or $C_{1-3}$ alkyl; and $R^8$ is H or $C_{2-4}$ alkanoyl which comprises:

(a) Reacting a chloroethenyl compound of the formula

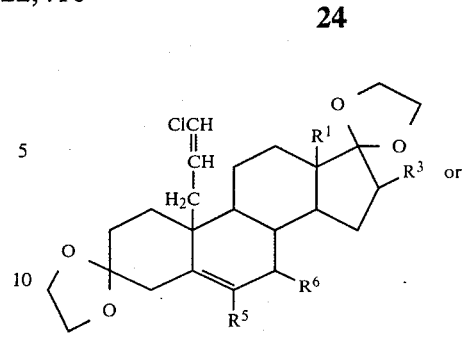

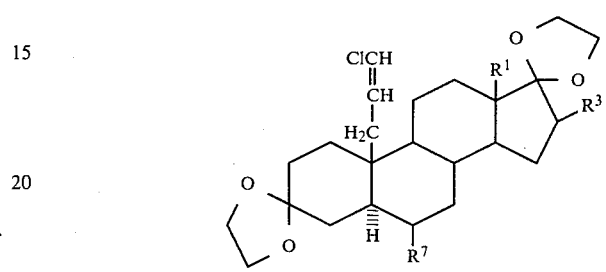

with a strong base in an inert solvent to give the corresponding 10-(2-propynyl) compound followed by treatment with acid to remove the protecting groups at the 3- and 17-positions, with shifting of any 5-unsaturation to the 4-position;

(b) Optionally followed by treatment with a dehydrogenating agent to introduce further unsaturation into the steroid nucleus;

(c) Optionally followed by hydride reduction to give the 17β-hydroxy compound and optional subsequent treatment with an appropriate acid derivative to give the corresponding 17β-ester.

23. A process according to claim 22 wherein the chloroethenyl compound is obtained by the reaction of the appropriate corresponding 19-carboxaldehyde with a phosphorane of the formula $(C_6H_5)_3P=CHCl$, the ethylenedioxy protecting groups at the 3- and 17-positions being optional during the reaction but, if absent, introduced by reaction of the 3,17-diketone with ethylene glycol in the presence of acid.

24. A process according to claim 22 for the preparation of 10-(2-propynyl)estr-4-ene-3,17-dione which comprises reacting 3,3,17,17-bis(ethylenedioxy)-10-(3-chloroprop-2-enyl)estr-5-ene with a strong base to give the corresponding 10-(2-propynyl) compound followed by treatment with acid to remove the protecting groups with shifting of the 5-unsaturation to the 4-position.

25. A process according to claim 24 wherein the 10-(3-chloroprop-2-enyl) compound is obtained by the reaction of 3,3,17,17-bis(ethylenedioxy)androst-5-ene-19-carboxaldehyde with $(C_6H_5)_3P=CHCl$.

* * * * *

UNITED STATES PATENT AND TRADEMARK OFFICE
CERTIFICATE OF CORRECTION

PATENT NO. : 4,322,416
DATED : March 30, 1982
INVENTOR(S) : Brian W. Metcalf and J. O'Neal Johnston It is certified that error appears in the above-identified patent and that said Letters Patent are hereby corrected as shown below:

Column 2, line 20, "effective" should read -- effected --.
Column 3, line 1, after "aromatase" delete the -- , --.
Column 3, lines 35-40; column 3, lines 47-52; column 4, lines 1-8; and column 4, lines 15-20, in the structural formulas,

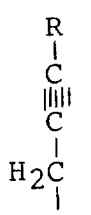   should read   

Column 4, lines 26-31, in the structural formula,

   should read   

Column 4, line 58, "R4" should read -- $R^4$ --.
Column 5, lines 56-61, in the structural formula,

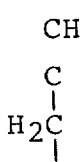   should read   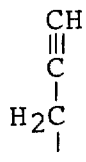

Column 6, line 10, in the chemical name, "(2-propynyl)5α-" should read -- (2-propynyl)-5α- --.
Column 6, line 12, in the chemical name, "(2-propynyl)5α-" should read -- (2-propynyl)-5α- --.

UNITED STATES PATENT AND TRADEMARK OFFICE
CERTIFICATE OF CORRECTION

PATENT NO. : 4,322,416
DATED : March 30, 1982
INVENTOR(S) : Brian W. Metcalf and J. O'Neal Johnston It is certified that error appears in the above-identified patent and that said Letters Patent are hereby corrected as shown below:

Column 7, lines 2-7, in the structural formula,

     should read     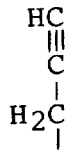

Column 7, line 52, "]cyclic" should read -- [cyclic --.
Column 7, line 56, after "acid" insert -- to --.
Column 8, lines 20-25, in the structural formula,

     should read     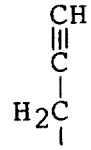

Column 8, line 37, after "treated with" delete -- the --.
Column 9, line 10, "$\Delta'$" should read -- $\Delta^1$ --.
Column 12, line 25, "competive" should read -- competitive --.
Column 13, line 22, "(p-Aminophenyl-" should read
-- (p-Aminophenyl)- --.
Column 15, line 29, "Dipmethylsiloxane" should read
-- Dimethylsiloxane --.
Column 16, line 8, "3,3,17-17-" should read -- 3,3,17,17- --.
Column 17, lines 4-9; column 18, lines 24-29; column 18, lines 45-50; column 19, lines 3-8; column 19, lines 25-30; column 19, lines 47-52; column 20, lines 2-7; column 20, lines 23-28; column 20, lines 53-58; column 21, lines 32-37; and, column 22, Claim 9, lines 47-52, in the structural formulas,

     should read     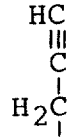

UNITED STATES PATENT AND TRADEMARK OFFICE
CERTIFICATE OF CORRECTION

PATENT NO. : 4,322,416
DATED : March 30, 1982
INVENTOR(S) : Brian W. Metcalf and J. O'Neal Johnston It is certified that error appears in the above-identified patent and that said Letters Patent are hereby corrected as shown below:

```
Column 20, line 17, "solidum" should read -- sodium --.
Column 21, line 15, "give" should read -- gives --.
Column 21, line 30, "-3,16,17-" should read -- -3,6,17- --.
Column 22, line 1, "Compound" should read -- Compounds --.
Column 22, line 15, under the structural formula, insert -- I --.
Column 22, line 25, under the structural formula, insert -- II --.
Column 22, line 40, after "wherein" insert -- --- --.
Column 23, line 9, "10(2-" should read -- 10-(2- --.
Column 23, lines 26-31 and column 23, lines 37-42, in the
structural formula,
```

   should read   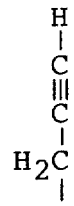

Signed and Sealed this

Seventeenth Day of January 1984

[SEAL]

Attest:

GERALD J. MOSSINGHOFF

Attesting Officer — Commissioner of Patents and Trademarks

UNITED STATES PATENT AND TRADEMARK OFFICE
CERTIFICATE OF CORRECTION

PATENT NO. : 4,322,416

DATED : March 30, 1982

INVENTOR(S) : Brian W. Metcalf & J. O'Neal Johnston

It is certified that error appears in the above-identified patent and that said Letters Patent are hereby corrected as shown below:

ON THE TITLE PAGE:

In the Abstract, line 4 after the structural formulas; column 3, line 63; and column 22, line 30, "5,6-bond" should read -- 6,7-bond --.

Signed and Sealed this

Twenty-fourth Day of November, 1987

Attest:

DONALD J. QUIGG

Attesting Officer

Commissioner of Patents and Trademarks